United States Patent [19]

Miyamori et al.

[11] Patent Number: 5,149,649
[45] Date of Patent: Sep. 22, 1992

[54] MULTI-LAYERED POROUS HOLLOW FIBER MEMBRANE FOR USE IN CELL CULTURE

[75] Inventors: Takao Miyamori; Makoto Uchida, both of Otake; Kanehiko Enomoto, Tokyo; Akihiro Sakimae, Otake; Ryozo Numazawa, Otake, all of Japan

[73] Assignee: Mitsubishi Rayon Co., Ltd., Tokyo, Japan

[21] Appl. No.: 561,323

[22] Filed: Aug. 1, 1990

[30] Foreign Application Priority Data

Aug. 4, 1989 [JP] Japan .................................. 1-201165
Oct. 9, 1989 [JP] Japan .................................. 1-263510

[51] Int. Cl.$^5$ .......................... C12N 5/00; B01D 39/00; C12M 1/04
[52] U.S. Cl. ............................. 435/240.242; 435/313; 435/285; 435/240.1; 210/500.21; 210/500.22; 210/500.29; 210/500.30
[58] Field of Search ............... 435/313, 314, 285, 286, 435/240.242, 240.1; 210/500.23, 500.29, 500.3

[56] References Cited

U.S. PATENT DOCUMENTS

| 4,826,599 | 5/1989 | Bikson | 210/500.3 |
| 4,853,128 | 8/1989 | Wrasidlo | 435/240.1 |
| 4,870,018 | 10/1989 | Lehmann | 435/240.1 |

FOREIGN PATENT DOCUMENTS

| 206354 | 12/1986 | European Pat. Off. . |
| 232975 | 8/1987 | European Pat. Off. . |
| 259109 | 3/1988 | European Pat. Off. . |
| 8703615 | 6/1987 | PCT Int'l Appl. . |

Primary Examiner—Douglas W. Robinson
Assistant Examiner—Jane A. Williams
Attorney, Agent, or Firm—Oblon, Spivak, McClelland, Maier & Neustadt

[57] ABSTRACT

A method for culturing cells by supplying oxygen to a culture medium through a multilayer composite membrane consisting of a porous layer(s) and a nonporous layer(s) having a thickness of less than 10 micrometers laminated one after the other. By using this multilayer composite membrane for supplying oxygen to the culture medium, oxygen can be supplied to the culture medium and/or the culture broth without causing foaming in the culture medium, cell growth inhibition or reduction in productivity of cellular products.

7 Claims, 3 Drawing Sheets

MULTI-LAYERED POROUS HOLLOW FIBER MEMBRANE FOR USE IN CELL CULTURE

BACKGROUND OF THE INVENTION

1. Field of the Invention

The present invention relates to a method for culturing animal, plant and microbial cells effectively.

2. Description of the Prior Art

Recently, production of beneficial substances by culturing animal, plant and microbial cells has been extensively carried out in fields of pharmaceutical, food and chemical industries and the like. In culturing these cells, an effective method for supplying oxygen to a culture medium or a culture broth is important.

Conventionally, in culturing cells, oxygen is supplied by a method in which gas containing oxygen, such as air, is directly introduced into a culture by sparging, namely by a method in which an orifice or a sintered filter is provided at a tip of an air blowing nozzle so that the size of gas bubbles is minimized as much as possible while stirring. Furthermore, a method in which oxygen partial pressure in a gas supplied or inner pressure in a culture device is increased so as to increase a rate of oxygen absorption into a culture has also been developed.

However, in these sparging methods, excessive foaming in a culture causes a problem. In particular, in culturing animal cells, excessive foaming in the culture medium or culture broth is caused by sparging because a culture medium frequently includes serum which contains proteins acting as a surface active agent; as a result, the cells growth is markedly inhibited. Furthermore, in culturing microbial cells, a volume of culture per culture bath has to be reduced because of foaming, which reduce productivity relative to the size of the culture bath. If the forming is excessively vigorous, culturing itself cannot be carried out.

Proposed methods for supplying oxygen more efficiently to cells in order to solve these problems include a method in which an aerobic cultivation of cells is carried out using porous hollow fiber (Japanese Patent Publication No. 7558/1982) and a method in which oxygen is supplied to a culture indirectly via a non-porous separating membrane made of silicone (Japanese Patent Publication No. 20261/1983, Japanese Patent Laid-open No. 309177/1988).

However, the porous membrane as disclosed in Japanese Patent Publication No. 7558/1982 is mechanically strong to some extent, when used for a long period of time, air bubbles may leak from the membrane due to change in blowing pressure, alternatively, membrane becomes hydrophilic due to the presence of surface active substances, thereby allowing the culture to permeate into a gas supplying part.

Furthermore, while the method disclosed in Japanese Patent Publication No. 20261/1983, in which a nonporous separating membrane is used, has an advantage that a culture medium or a culture broth does not permeate into the inside of the hollow fibers; because the oxygen diffusion resistance of the membrane is high, it is necessary to enlarge a membrane area enormously or to use a extremely thin membrane having low diffusion resistance in order to supply sufficient oxygen for the growth of cells. However, such a method which can supply enough oxygen for the cell growth by enlarging the membrane area is not economically advantageous because the amount of the membrane to be used increases excessively.

Furthermore, in the method disclosed in Japanese Patent Laid-open No. 309177/1988, in which a thin silicone-made nonporous separating membrane is used, it is necessary to employ a complicated method of making the silicone-made nonporous separating thin membrane having weak mechanical strength in a form of net, in order to maintain its mechanical strength and to protect the hollow fiber membrane from being torn by unexpected force.

Furthermore, when used as a membrane module, the membrane has to be immobilized at the end using a potting agent; however, adhesion of the nonporous separating membrane to the potting agent is weak because the surface of the membrane is not rough enough. Therefore, the surface of the membrane has to be treated in advance to make the surface rough, which complicates a process for producing the membrane module. Furthermore, when the membrane is practically used in cultivation, the thin membrane which has substantially effective oxygen permeability is mechanically weak and easily smashed by pressure due to cell growth, which results in reduction in gas permeability or destruction of the membrane.

SUMMARY OF THE INVENTION

An object of the present invention is to solve the problems described above: that is to provide a method for culturing cells effectively by using an oxygen permeable membrane capable of supplying necessary oxygen sufficient for cell growth to a culture medium or a culture broth, which prevents (a) foaming in the culture medium or the culture broth, growth (b) inhibition of cells and reduction (c) in productivity of cellular products.

As a result of intensive study, the present inventors have found that the above-mentioned problems can be solved by using a multilayer composite membrane consisting of a nonporous layer(s) and a porous layer(s).

Namely, the present invention provides a method for culturing cells by supplying oxygen to a culture medium and/or a culture broth via a membrane structure, a multilayer composite membrane, in which a porous layer(s) and a nonporous layer(s) having a thickness of 10 micrometers or less are laminated one after the other.

According to the present invention, oxygen can be supplied to a culture medium or a culture broth without causing foaming in the culture medium or the culture broth, inhibition of cell growth and reduction in productivity of cellular products. Through the use of the present invention effective cultivation of aerobic microorganisms or animal or plant cells can be carried out.

DETAILED DESCRIPTION OF THE INVENTION AND PREFERRED EMBODIMENTS

Figure 1:
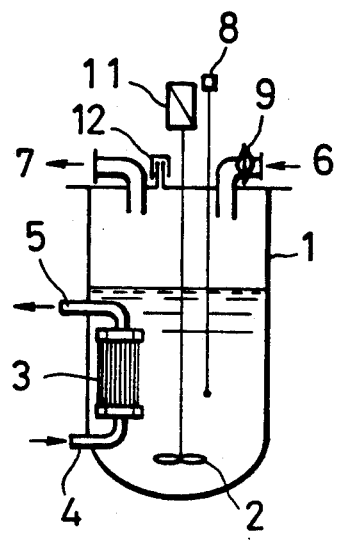
FIGS. 1, 2, 3 and 5 are graphic drawings illustrating examples of culture baths and culture devices to be used according to the present invention.

A method for culturing cells according to the present invention comprising a step of culturing cells by supplying oxygen to a culture medium and/or a culture broth via a membrane, said membrane being a multilayer composite membrane in which a porous layer(s) and a nonporous layer(s) having a thickness of 10 micrometers or less are laminated one after the other.

Cells to which a cultivation method of the present invention is applicable include animal, plant and insect cells, cells of aerobic microorganisms and protozoan which grow aerobically.

Furthermore, a culture medium in the present invention denotes generally a liquid which contains nutrient sources necessary for growth of the cells and production of substances, and a culture broth denotes a liquid comprising the above-mentioned culture medium and cells to be cultured.

A multilayer composite membrane denotes a membrane in which a nonporous layer(s) and a porous layer(s) are laminated one after the other so that the porous layer(s) fortify the mechanical strength of the nonporous layer(s). In the multilayer composite membrane, the number of layers in the laminated construction are not specifically limited if the above-mentioned conditions are satisfied; however, it is preferable that at least one side of the outer surface of the multilayer composite membrane is a porous layer. Representative examples include a three-layered construction in which a nonporous layer is placed between two porous layers and a two-layered construction in which a nonporous layer and a porous layer are laminated. Furthermore, the nonporous layer may consist of two or more layers and thus a laminated construction having four or more layers as a whole may be constructed.

In case that the multilayer composite membrane having a porous layer at least on one side of its surfaces is set into a membrane module by immobilizing the membrane at its end with a potting agent, the multilayer composite membrane can be closely adhered with the potting agent so that the process for making the membrane module is simplified. The thickness of the porous layer may be the same or different one another; however, the thickness of the multilayer composite membrane is preferably 10 micrometers or more in view of mechanical strength and desirably 100 micrometers or less in view of the necessity to enlarge the membrane area relative to the unit volume.

Furthermore, it is preferable to use a multilayer composite membrane having a rate of oxygen permeability of $1 \times 10^{-5}$ [cm$^3$(STP)/cm$^2$·sec·cmHg] or more.

Any materials having excellent oxygen permeability can be used in making the nonporous layer in the multilayer composite membrane. Examples include various kinds of polymers such as, e.g. silicone gum homopolymers; polydimethylsiloxane; silicone-polycarbonate copolymers; polyolefin polymer such as poly-4-methylpentene-1 and low density linear polyethylene; fluoride polymers such as perfluoroalkyl polymers; cellulose polymers such as ethylcellulose; polyphenylene oxide; poly-4-vinylpyridine; segmented polyurethane; copolymers of these polymer materials; and blends thereof.

The thickness of the nonporous layer is 10 micrometers or less in consideration of oxygen permeability, more preferably 5 micrometers or less, or preferably 1 micrometer or less.

Furthermore, the thickness of the porous layer in the above-mentioned multilayer composite membrane is preferably 1 to 30 micrometers in consideration of mechanical fortification and protective function. Materials for the porous layer include hydrophobic polymers such as polyolefin polymers such as polyethylene, polypropylene, poly-3-methylbutene-1 and poly-4-methylpentene1; fluoride polymers such as polyvinylidene fluoride and polytetrafluoroethylene; polystylene; and polyetheretherketone. However, material to be used are not limited to hydrophobic polymers but hydrophilic polymers may also be used. Among these materials, polyolefin polymers are preferably used.

An example of the combination of the materials is polyethylene or polypropylene for the porous layer and segmented polyurethane for the nonporous layer, or poly-4-methylpentene-1 for the porous layer and silicone-polycarbonate copolymers for the nonporous layer.

It is preferable to use heat resistant materials such as poly-4-methylpentene-1 for the porous layer in consideration that a cell culture vessel is sterilized for use repeatedly by steam sterilization.

The shape of the multilayer composite membrane may be in a form of a flat membrane, a hollow fiber or the like; however, the membrane in a form of a hollow fiber is particularly preferable.

The multilayer composite membrane can be obtained by various methods; however, it is preferable to be obtained by processes of melt-spinning and stretching process because these processes can provide thin layered nonporous layers and porous layers having high mechanical strength. An example of these processes is disclosed in Japanese Patent Laid-open No. 1404/1987 or U.S. Pat. No. 4,713,292.

According to the above-mentioned method, a multilayer composite hollow fiber membrane having slit like pores in the porous layer and the slit like pores are interconnected so as to make tortous paths from one surface to the other surface and have major axis extended in the axial direction of the fiber.

In the use of the above-mentioned multilayer composite membrane, a membrane module which is generally used in an artificial kidney, lung or the like is advantageously used; namely, the membrane may be laminated in several layers in case of a flat membrane, or several fibers may be bundled and immobilized at the end in case of a hollow fiber membrane. Furthermore, the resulting membrane module can be brought into contact with a gas containing oxygen at one surface of the membrane and with a culture medium or a culture broth at the other surface so as to supply oxygen to the culture medium or the culture broth. In case of the hollow fiber membrane, it is possible to supply oxygen to the culture medium or the culture broth outside the hollow fiber by feeding gas into the hollow parts, i.e. inside, of the hollow fiber, or supply oxygen to the culture medium or the culture broth inside of the hollow fiber by feeding gas to the outer surface of the hollow fiber.

As for a method for supplying oxygen to a culture medium or a culture broth using the multilayer composite membrane, various methods are applicable. For example, a multilayer composite membrane to supply oxygen is installed apart from a cell culture bath so that oxygen is supplied by passing a culture medium or a culture broth through the membrane module. It is also possible to install the membrane module inside the culture bath so that the membrane module is sintered in the culture broth and thus oxygen is supplied to the culture broth. Furthermore, the membrane module using a multilayer composite membrane is made in various forms in compliance with the culture method or the shape of culture bath to be used.

Further, in culturing cells using the multilayer composite membrane module, the membrane module is preferably sterilized by gas sterilization using ethylene oxide, steam sterilization or the like.

Furthermore, any kinds of gas which contain oxygen can be used in culturing cells; a gas mixture containing oxygen, air, nitrogen, carbon dioxide gas or the like at an arbitrary ratio can be used.

The present invention will be explained hereinafter in more detail by reference to the accompanying drawings. FIG. 1 shows an example of a cell culture device to practice the present invention. The number 1 is a culture bath into which a culture medium and suspending cells are put; the number 2 is a stirring propeller to stir the culture broth; the number 3 is a multilayer composite hollow fiber membrane module to supply oxygen to the culture broth, which is connected to pipes at both ends each leading to a gas inlet 4 and a gas outlet 5. The number 6 is an inlet for $CO_2$ gas supply and the number 7 is an outlet for exhaust gas. This device is so constructed that cells in the culture broth are evenly suspended by the stirring propeller, and oxygen gas necessary for growth of the cells is introduced into the inside (hollow parts) of each the multilayer composite hollow fiber membrane via the gas inlet 4 and then transferred to the culture broth through the membranes. Thereby, sufficient oxygen for the cell growth can be supplied to the culture broth without foaming.

Figure 2:
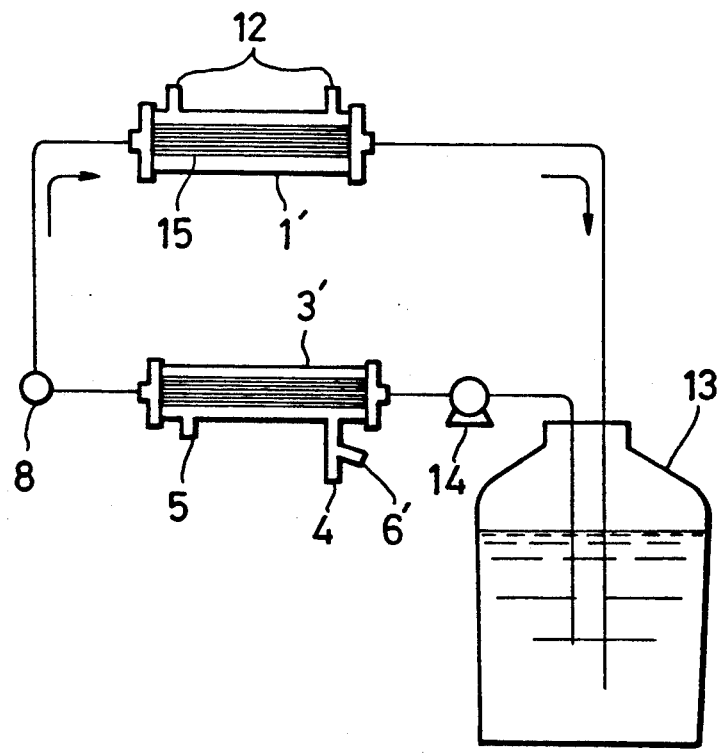

FIG. 2 shows a cell culture device in which a multilayer composite membrane module and a cell culture bath are installed independently. In this device, a culture medium is circulated in the system by a pump 14. The culture medium flows inside each the multilayer composite hollow fiber membrane, i.e. each hollow part, and oxygen introduced from the gas inlet 4 is supplied to the culture medium. $Co_2$ is supplied through inlet 6'. A porous hollow fiber membranes 15 are placed in a culture bath 1', cells are inoculated from a cell inoculation port 12 outside the porous hollow fiber membranes, whereas the culture medium flows hollow parts (inside) of the porous hollow fiber membranes, supplying nutrients and oxygen to the cells outside the porous hollow fiber membranes through their porous walls.

Figure 3:
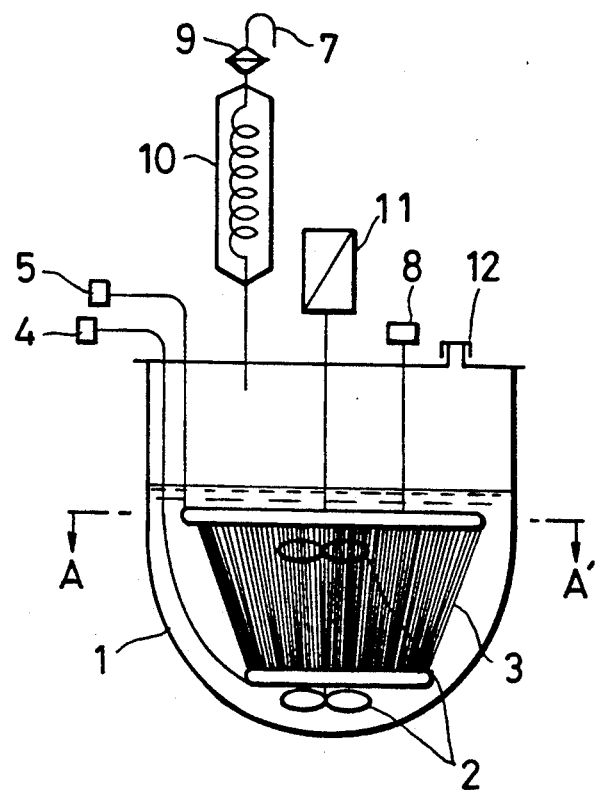
Figure 4:
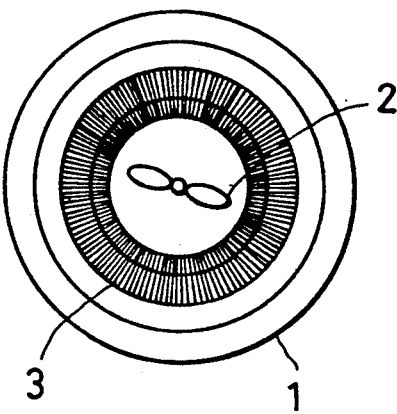
FIGS. 4 and 6 are cross-sectional views taken on line A-A' of FIG. 3 and line line B-B' of FIG. 5, respectively.

FIGS. 3 and 4 individually show a cell culture device in which the shape of the multilayer composite hollow fiber membrane module suitably fits to the shape of the culture bath. These membrane modules are formed in the forms of top-chopped cone and cylinder with a hollow in the center, respectively; a condenser 10 for exhausting gas is installed upward the culture bath.

Application of the oxygen supplying method according to the present invention is not limited to the ordinary cultivation of aerobic microorganisms, animal and plant cells and the like but expanded to cell cultivation in which cells are immobilized on the surface of a carrier or cell cultivation in which cells grow inside a carrier using microcarriers and microcapsules, so as to produce beneficial substances.

The present invention will be further explained referring to the following examples.

EXAMPLE 1

A membrane module having an effective membrane area of 200 cm$_2$ was constructed by bundling multilayer composite hollow fiber membranes having a three-layer structure as shown in Table 3 was installed in a one liter volume culture bath shown in FIG. 1; mouse myeloma cells, MPC-11 strain (ATCC CCL167), were incubated in the bath under the following conditions:

A medium (hereinafter referred to as RDF medium) was prepared by adding 10% (w/v) newborn calf serum, 4 mM glutamine, 25 micrograms/ml streptomycin, 25 U/ml penicillin, 16 mM HEPES buffer solution and 0.01% (w/v) sodium hydrogencarbonate to a basal medium in which RPMI-1640 medium (a product of Nissui Seiyaku Co.), DME medium (Dulbecco Modified Eagle's medium, a product of Nissui Seiyaku Co.) and Ham F12 medium (a product of Flow Laboratories) are mixed at a ratio of 2:1:1 (v/v), pH being adjusted to 7.0, 450 ml of the medium was put into the above-mentioned culture bath, and then 50 ml of precultured cells of MPC-11 strain ($5.0 \times 10^5$ cells/ml, having 93% viability) was inoculated into the medium.

Subsequently, air is introduced at a rate of 100 ml/min into the inside of the hollow part of each multilayer composite hollow fiber membrane from the gas inlet 4, and incubation was carried out for 72 hours while stirring using the stirring propeller at 60 rpm. Further, during the incubation, $CO_2$ gas was blown from the gas supplying inlet 6 to maintain pH of the culture broth at 7.0.

The cell density at the end of the cultivation was $6.8 \times 10^6$ cells/ml and the viability of the cells was 95%. Furthermore, no foaming was observed during the incubation.

COMPARATIVE EXAMPLE 1

Cultivation was carried out in the same manner of Example 1 except that a membrane module having an effective membrane area of 200 cm$^2$ and using the silicone gum hollow fibers having the properties shown in Table 2, was used in place of the multilayer composite hollow fiber membrane module having the three-layer construction. After 72 hours, the cell density was $2.3 \times 10^6$ cells/ml and the viability was 85%.

EXAMPLE 2

Cell cultivation was carried out in the same manner as described in Example 1 except that multilayer composite hollow fiber membranes having the three-layer construction shown in Table 1 were used in place of the multilayer composite hollow fiber membranes having the three-layer construction shown in Table 3.

At the end of the cultivation, the cell density was $5.6 \times 10^6$ cells/ml and the viability of the cells was 87%. Furthermore, no foaming was observed during the cultivation.

EXAMPLE 3

Cells of MPC-11 strain cultured in the medium having the same medium composition as in Example 1 was suspended in a physiological saline solution containing 2% sodium alginate to obtain the cell density of $6.0 \times 10^5$ cells/ml. The suspension was put into a syringe and dropped into a physiological saline solution containing 2% calcium chloride. In this way, cells were incorporated into spherical capsules (microcapsules, about 600 micrometers in diameter) made of sodium alginate. The cell density in the capsules was $5.4 \times 10^5$ cells/ml and the viability of the cells was 88.0%.

The capsules were filtered and washed with RDF medium supplemented with 0.1% (w/v) poly-L-lysine. Subsequently, 50 ml of the content of the above-mentioned washed capsule and 450 ml of RDF medium were put into the culture bath as in Example 2 and incubation was carried out at 37° C. for 14 days. During the incubation air was blown into the bath at 100 ml/min and $CO_2$ gas was supplied to maintain the pH at 7.0.

At the end of the cultivation the cell density in the capsules was $2.0 \times 10^8$ cells/ml and viability of the cells was 76%.

EXAMPLE 4

The composite hollow fiber membranes having the three-layer construction shown in Table 1 were placed in a polycarbonate-made cylindrical vessel to make a multilayer composite membrane module (oxygen enriching device with a container having an effective membrane area of 1,000 cm²).

Separately, a porous polyethylene hollow fiber membranes (a product of Mitsubishi Rayon Co., Ltd., EHF 270T, 270 micrometers in diameter, 55 micrometers thick and 72% in propsity) was placed into a poly-carbonate-made cylindrical vessel (culture, bath) to make a cell culture device having a outer volume of the hollow fiber membranes of 100 cm³.

The oxygen enriching device and the cell culture device are sterilized and then assembled with a culture medium reservoir 13 in a clean box into a system as shown in FIG. 2 and then the system was placed in an incubator at 37° C.

Subsequently, 3 liters of a culture medium consisting of Ham F12 (90%) and fetal calf serum (10%) was put into a culture medium reservoir 13 and circulated in the system using a pump 14. Furthermore, $1 \times 10^7$ clls of CHO-K1 (ATCC CCL-61, derived from chinese hamster ovary cells) which had been precultured was asceptically inoculated from a cell inoculation opening 12 and then incubation was started.

During the incubation, air was supplied from a gas inlet 4 at a rate of 100 ml/min and, when a pH value measured by a pH sensor 8 exceeded 7.4, carbon dioxide gas was supplied from a $CO_2$ gas supplying inlet 6' and mixed with the supplying gas to maintain the pH 7.4 or less.

The culture medium was circulated in the system at a rate of 100 ml/min and after day 4, the whole medium was exchanged with a fresh medium every 2 days. The incubation was carried out for 10 days. During the incubation, foaming was not observed. After 10 days, the amount of cells in the culture bath 1' was $1.4 \times 10^9$.

COMPARATIVE EXAMPLE 2

Incubation was carried out in the same manner as in Example 4 except that polypropylene-made porous hollow fiber membranes (a product of Mitsubishi Rayon Co., Ltd., KPF 190M) were used instead of the three-layer composite hollow fiber membranes. From day 3, foaming was observed in the culture of the oxygen enriching device 3', and on and after day 5, air bubbles were accumulated in the culture bath 1' (cell culture device) and culturing efficiency was decreased; as a result, the amount of the cells after 10 days of cultivation was $8.5 \times 10^8$.

EXAMPLE 5

The cells were incubated in the same manner as described in Example 4 except that the oxygen enriching vessel was made by filling a multilayer composite hollow fiber membranes having the three-layer construction described in Table 3 in a polycarbonate cylindrical vessel so as to make a membrane area of 1000 cm². After 10 days, the number of the cells in the culture bath 1' was $2.9 \times 10^9$.

EXAMPLE 6

The surface of a bulk of a Lilium auratum was sterilized with a 70% ethyl alcohol aqueous solution and a 10% sodium hydrochlorite aqueous solution and then cut into pieces of 5 mm–15 mm squares. One piece each was placed in a test tube (2.5 cm in diameter and 12.5 cm in depth) containing 10 ml of Murashige-Skoog solid agar medium (pH 6.2) as shown in Table 4 and cultured at 25° C. under irradiation of 2,500 luxes for 60 days. After the incubation 1–5 calluses per one piece differentiated from the bulb was obtained. 150 pieces of ramenta thus obtained was collected and sterilized with sodium hydrogenchlorite for 15 minutes and then thoroughly washed.

Separately, a top-chopped cone shaped membrane module having a hollow in the middle having an effective membrane area of 1 m², which was constructed using the multilayer composite hollow fiber membranes shown in Table 1, was placed in the culture bath 1 as shown in FIG. 3, and then 2 liters of a culture medium having the composition shown in Table 4 without agar, supplemented with abscisic acid (0.2 mg/l), was put into the culture bath and further the above-mentioned ramenta were transplanted.

Cultivation was carried out at 25° C. for 50 days under the continuous irradiation of 5,000 luxes. During the cultivation air was supplied from the gas inlet into the hollow part of each the multilayer composite hollow fiber membrane at a rate of 1 liter/min, while stirring by a stirring propeller at 30 rpm. At a result about 2,000 bulbs were obtained.

EXAMPLE 7

Cells of *Pseudomanas putida* (ATCC 8209) was inoculated into 100 ml of a liquid culture medium (pH 6.8) consisting of 0.5% meat extract, 0.75% peptone, 0.25% NaCl, 0.5% glucose, 0.15% malto-extract and 0.15% yeast extract, and incubation was carried out at 30° C. for 1 day with shaking. A mixed culture consisting of 25 ml of the resulting culture broth and 1975 ml of 30-fold diluted corn steep liqueur (a product of Oji Corn Starch Inc.) was obtained and further supplemented with 4.0% glucose, 0.75% ammonium sulfate and 0.1% yeast extract.

Figure 5:
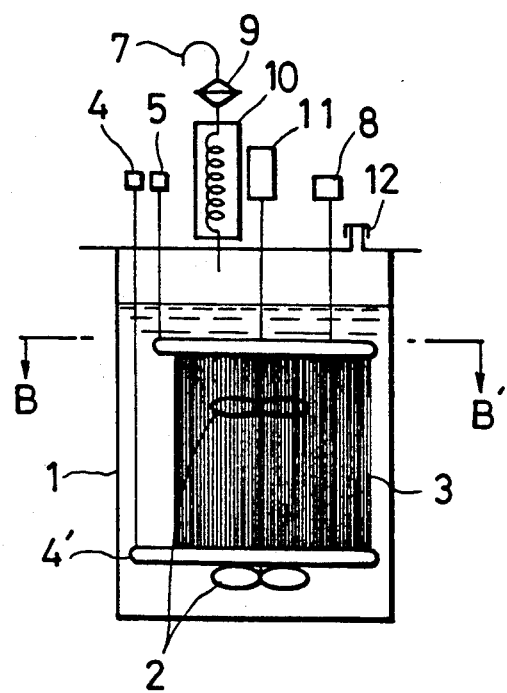
Figure 6:
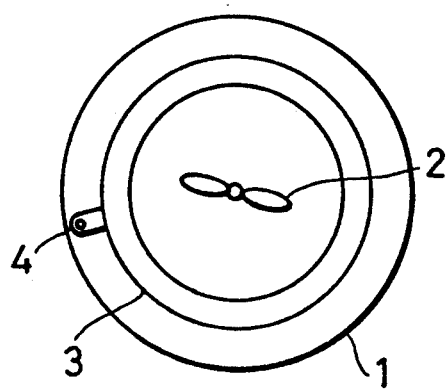

Separately, a cylindrical membrane module (having an effective area of 1 m²) was constructed using the multilayer composite hollow fiber membranes shown in Table 1 and placed in the culture bath 1 as shown in FIG. 5; 2 liters of the above-mentioned culture broth was put into the culture bath and then incubation was set up.

During the incubation, air was supplied from the gas inlet at 1 liter/min while string with the stirring propeller at 300 rpm and maintaining the temperature of the fluid at 30° C. and the pH of the fluid at 7.0 using a 10% NaOH solution or a 10% $H_2SO_4$ solution.

After 24 hours, glucose was added at a concentration of 4% and the incubation was continued for another 24 hours. No anti-foaming agent was added to the culture medium but foaming was not observed during the incubation. The cell concentration at the end of the incubation was 18 g/l in dry weight.

COMPARATIVE EXAMPLE 4

Incubation was carried out in the same manner as in Example 6, except that the polypropylene-made porous hollow fiber membranes (a product of Mitsubishi Rayon Co., Ltd., KPF 190M) were used in place of the module using the multilayer composite hollow fiber membranes having the three-layer construction. After 20 hours, air foaming began from the hollow fibers in the culture broth. At 24 hours after the beginning of the incubation, glucose was added at a concentration of 4% and the incubation was continued. After 30 hours, foaming was vigorous and the condenser 10 and the bacteria repellent filter 9 got wet because of the foaming, so that the incubation was terminated at 35 hours after the beginning of incubation. A cell concentration at this time was 11 g/l in dry weight.

EXAMPLE 8

Cultivation was carried out in the same manner as in Example 4 except that the polycarbonatemade cylindrical vessel was filled with the multilayer composite hollow fiber membranes having the three-layer structure shown in Table 5 so as to make an oxygen enriching device having an effective area of 1,000 cm$^2$. After 10 days of the incubation, the cell numbers in the culture bath was $1.9 \times 10^9$.

TABLE 1

|  | Porous layer (outer and inner layers) | Nonporous layer (median layer) |
|---|---|---|
| Material | High-density polyethylene | Segmented polyurethane |
| Thickness | 30 micrometers | 0.5 micrometer |
| Inside diameter | 200 micrometers | |
| Rate of oxygen permeation (cm$^3$/cm$^2$ · sec · cmHg) | $1.2 \times 10^{-5}$ | |

TABLE 2

| Material | Dimethlsiloxane silicone gum |
|---|---|
| Thickness | 100 micrometers |
| Inside diameter | 200 micrometers |
| Rate of oxygen permeation (cm$^3$/cm$^2$ · sec · cmHg) | $6.0 \times 10^{-6}$ |

TABLE 3

|  | Porous layer (outer and inner layers) | Nonporous layer (median layer) |
|---|---|---|
| Material | Poly-4-methylpentene-1 (a product of Mitsui Petroleum Chemicals, Inc., TPX MX007) | Silicone-polycarbonate copolymer (a product of GE, Copel LR3320) |
| Thickness | 30 micrometers | 0.5 micrometer |
| Inside diameter | 200 micrometers | |
| Rate of oxygen permeation (cm$^3$/cm$^2$ · sec · cmHg) | $1.0 \times 10^{-4}$ | |

TABLE 4

| Ammonium nitrate | 1650 mg/l |
|---|---|
| Potassium nitrate | 1900 mg/l |
| Calcium chloride.2H$_2$O | 440 mg/l |
| Magenesium sulfate.7H$_2$O | 370 mg/l |
| Potassium dihydrogenphosphate | 170 mg/l |
| Na$_2$.EDTA.2H$_2$O | 37.3 mg/l |
| Iron (II) sulfate.7H$_2$O | 27.8 mg/l |
| Boric acid | 6.2 mg/l |
| Manganese sulfate.4H$_2$O | 22.3 mg/l |
| Zinc sulfate.7H$_2$O | 8.6 mg/l |
| Sucrose | 30 g/l |
| Potassium iodide | 0.83 mg/l |
| Sodium molybdate | 0.25 mg/l |
| Copper (I) sulfate | 0.025 mg/l |
| Cobalt chloride | 0.025 mg/l |
| Vitamin B$_1$ | 0.40 mg/l |
| Inositol | 100 mg/l |
| Pyridoxine chloride | 0.5 mg/l |
| Nicotinic acid | 0.5 mg/l |
| Glycine | 2.0 mg/l |
| Naphthaleneaceti acid | 0.1 mg/l |
| Agar | 10 g/l |

TABLE 5

|  | Porous layer (outer and inner layers) | Nonporous layer (median layer) |
|---|---|---|
| Material | Poly-4-methylpentene-1 (a product of Mitsui petroleum Chemicals, Inc., TPX MX007) | Silicone polycarbonate copolymer (a product of GE, Copel LR3320) |
| Thickness | 30 micrometers | 2.5 micrometers |
| Inside diameter | 200 micrometers | |
| Rate of oxygen permeation (cm$^3$/cm$^2$ · sec · cmHg) | $2.0 \times 10^{-5}$ | |

What is claimed is:

1. A method for culturing cells by supplying oxygen to a culture medium and/or culture broth through a hollow fiber membranous structure, wherein said membranous structure is a multi-layer composite membrane which consists of two porous layers, having slit-like pores, on both the surfaces and a non-porous layer having a thickness of 10 micrometers or less in a median layer, and wherein said layers are laminated one after the other.

2. A method as set forth in claim 1, which is characterized in that a rate of oxygen permeation of the multilayer composite membrane is $1 \times 10^{-5}$ [cm$^3$(STP)/cm$^2$·sec·cmHg] or more.

3. A method as set forth in claim 1, wherein the nonporous layer of the multilayer composite membrane is 5 or less micrometers thick.

4. A method as set forth in claim 1, wherein a material for the porous layers of the multilayer composite membrane is a polyolefin polymer or fluoride polymer.

5. A method as set forth in claim 1, wherein a material for a porous layer of the multilayer composite membrane is poly-4-methylpentene-1.

6. A method as set forth in claim 1, wherein a material for the nonporous layer in the multilayer composite membrane is selected from the group consisting of segmented polyurethane, polyphenylene oxide, poly-4-vinylpyridine, silicone gum polymers, silicon polycarbonate copolymers, polyolefin polymers and fluoride polymers.

7. A method as set forth in claim 1, wherein the cells are aerobic microorganisms or plant or animal cells.

* * * * *